United States Patent
Schober et al.

(10) Patent No.: US 9,806,591 B2
(45) Date of Patent: Oct. 31, 2017

(54) LINEAR DEVICE AND ELECTRIC DEVICE WITH LINEAR MOTOR

(71) Applicant: Braun GmbH, Kronberg (DE)

(72) Inventors: Uwe Schober, Glaushutten (DE); Frank Ziegler, Karben (DE); Robert Schaefer, Frankfurt (DE)

(73) Assignee: BRAUN GMBH, Kronber (DE)

(*) Notice: Subject to any disclaimer, the term of this patent is extended or adjusted under 35 U.S.C. 154(b) by 1027 days.

(21) Appl. No.: 13/939,198

(22) Filed: Jul. 11, 2013

(65) Prior Publication Data

US 2014/0015346 A1 Jan. 16, 2014

(30) Foreign Application Priority Data

Jul. 13, 2012 (EP) ..................................... 12176403

(51) Int. Cl.
| | |
|---|---|
| *H02K 33/00* | (2006.01) |
| *F16F 1/18* | (2006.01) |
| *A61C 17/34* | (2006.01) |
| *H02K 33/16* | (2006.01) |
| *A61C 17/22* | (2006.01) |

(52) U.S. Cl.
CPC ........... *H02K 33/00* (2013.01); *A61C 17/225* (2013.01); *A61C 17/3436* (2013.01); *F16F 1/18* (2013.01); *H02K 33/16* (2013.01)

(58) Field of Classification Search
CPC ..... H02K 33/00–33/18; A61C 17/3436; A61C 17/34–17/3481
USPC ................................. 310/12.01–12.33, 15–19
See application file for complete search history.

(56) References Cited

U.S. PATENT DOCUMENTS

| | | | |
|---|---|---|---|
| 6,760,945 B2* | 7/2004 | Ferber ................. | A61C 17/224 15/22.1 |
| 7,067,945 B2* | 6/2006 | Grez .................. | A61C 17/3418 15/22.1 |
| 2004/0128781 A1* | 7/2004 | Kunita ............... | A61C 17/3445 15/22.2 |
| 2004/0130221 A1 | 7/2004 | Ichii et al. | |
| 2005/0200207 A1* | 9/2005 | Hasegawa ............. | H02K 33/16 310/10 |
| 2006/0066154 A1 | 3/2006 | Ogino et al. | |
| 2006/0255665 A1* | 11/2006 | Kraus .................... | H02K 33/18 310/36 |

(Continued)

FOREIGN PATENT DOCUMENTS

| | | | | |
|---|---|---|---|---|
| JP | WO 2013084438 A1 * | 6/2013 | ............. | H02K 33/16 |
| WO | WO 2005/006538 A1 | 1/2005 | | |

OTHER PUBLICATIONS

Machine Translation, Moriguchi et al., WO 2013084438 A1, Jun. 13, 2013.*

*Primary Examiner* — Thomas Truong

(57) ABSTRACT

A linear motor is disclosed. The linear motor includes an armature mounted for driven linear oscillation substantially along a longitudinal direction; a secondary mass mounted for linear oscillation substantially along the longitudinal direction; and a coupling unit for coupling the armature and the secondary mass. The coupling unit includes at least two coupling spring assemblies and at least a coupling element, the coupling spring assemblies being arranged in planes perpendicular to the longitudinal direction and being spaced apart from each other, and the coupling element being fixedly connected with the coupling spring assemblies.

16 Claims, 6 Drawing Sheets

(56) References Cited

U.S. PATENT DOCUMENTS

2011/0214239 A1* 9/2011 Kagami ............... A61C 17/32
                                              15/22.1
2012/0207628 A1* 8/2012 Al Otaibi ............. H02K 33/16
                                              417/415

* cited by examiner

A - A

LINEAR DEVICE AND ELECTRIC DEVICE WITH LINEAR MOTOR

FIELD OF THE INVENTION

The present disclosure is directed to a linear motor. More particularly, the present disclosure is directed to a linear motor comprising a secondary mass. The invention is further directed to an electric device comprising such a linear motor.

BACKGROUND OF THE INVENTION

Linear motors are known that comprise a casing, an armature mounted at the casing for linear oscillation, a stator comprising a coil for driving the armature into oscillatory motion, and an amplitude control spindle, where the armature is at one end biased with a coil spring against the casing, the amplitude control spindle is biased at one end by a coil spring against the casing, and where the other end of the armature is biased by a coil spring against the other end of the amplitude control spindle. The amplitude control spindle is in particular used to absorb or increase an amplitude of the armature. Document US 2004/130221 A1 generally discusses such a motor.

SUMMARY OF THE INVENTION

In one embodiment, a linear motor is provided. The linear motor includes an armature mounted for driven linear oscillation substantially along a longitudinal direction; a secondary mass mounted for linear oscillation substantially along the longitudinal direction; and a coupling unit for coupling the armature and the secondary mass. The coupling unit includes at least two coupling spring assemblies and at least a coupling element, the coupling spring assemblies being arranged in planes perpendicular to the longitudinal direction and being spaced apart from each other, and the coupling element being fixedly connected with the coupling spring assemblies.

In another embodiment, a linear motor is provided. The linear motor includes an armature mounted for driven linear oscillation essentially along a longitudinal direction; and a drive shaft being driven by the armature into a linear oscillation along a first longitudinal axis that is parallel to the longitudinal direction. The armature is asymmetrically arranged with respect to the longitudinal axis and has two opposing end parts extending along the first longitudinal axis, a center part including a permanent magnet arrangement, which center part extends in longitudinal direction with an offset to the first longitudinal axis, and two connecting parts that each connect one of the end parts with the center part.

In another embodiment, a linear motor is provided. The linear motor includes an armature mounted for driven linear oscillation essentially along a longitudinal direction; and at least a first armature mounting spring assembly arranged in a mounting plane perpendicular to the longitudinal direction. The first armature mounting spring assembly is shaped such that it fits into a circle approximating the shape of a half of the first armature mounting spring assembly in the mounting plane, where at least a first section of the circle can be cut away, which first section does not comprise a part of the first armature mounting spring assembly. The height of the first section being at least about 10% of the diameter of the circle.

In another embodiment, a flat leaf spring for a linear motor is provided. The leaf spring includes, an inner fastening section; an outer fastening section; and a spring arm connecting the inner fastening section and the outer fastening section. The flat leaf spring is made from a single sheet such that the inner fastening section, the spring arm, and the outer fastening section are integral with each other. The spring arm spirals around the center of area of the inner fastening section and the flat leaf spring is oblate in its plane of extension such that a ratio between a width of the leaf spring and a height of the flat leaf spring has a value of at least about 1.33. The direction in which the height is measured being perpendicular to the direction in which the width is measured.

In another embodiment, a flat leaf spring is provided. The leaf spring includes, an inner fastening section, an outer fastening section, and a spring arm connecting the inner fastening section and the outer fastening section. The flat leaf spring is made from a single sheet such that the inner fastening section, the spring arm, and the outer fastening section are integral with each other. The spring is shaped such that it fits into a smallest rectangle enveloping the spring in its plane of extension, the rectangle having a ratio between its width and its height of at least about 1.33.

In yet another embodiment, an oral hygiene device with a resonant linear motor for providing a linear oscillatory movement along a longitudinal direction is provided. The oral hygiene device includes a housing; a stator comprising a coil core and a stator coil wound around the coil core, which stator is fixedly mounted at or with respect to the housing; an armature comprising a permanent magnet arrangement, which armature is mounted for linear oscillatory movement along the longitudinal direction relative to the stator; and a drive shaft coupled with the armature, the drive shaft centrically extending along a longitudinal axis parallel to the longitudinal direction. The armature has two opposite end sections that are disposed at the longitudinal axis and a central section carrying the permanent magnet arrangement, which central section is offset from the longitudinal axis.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
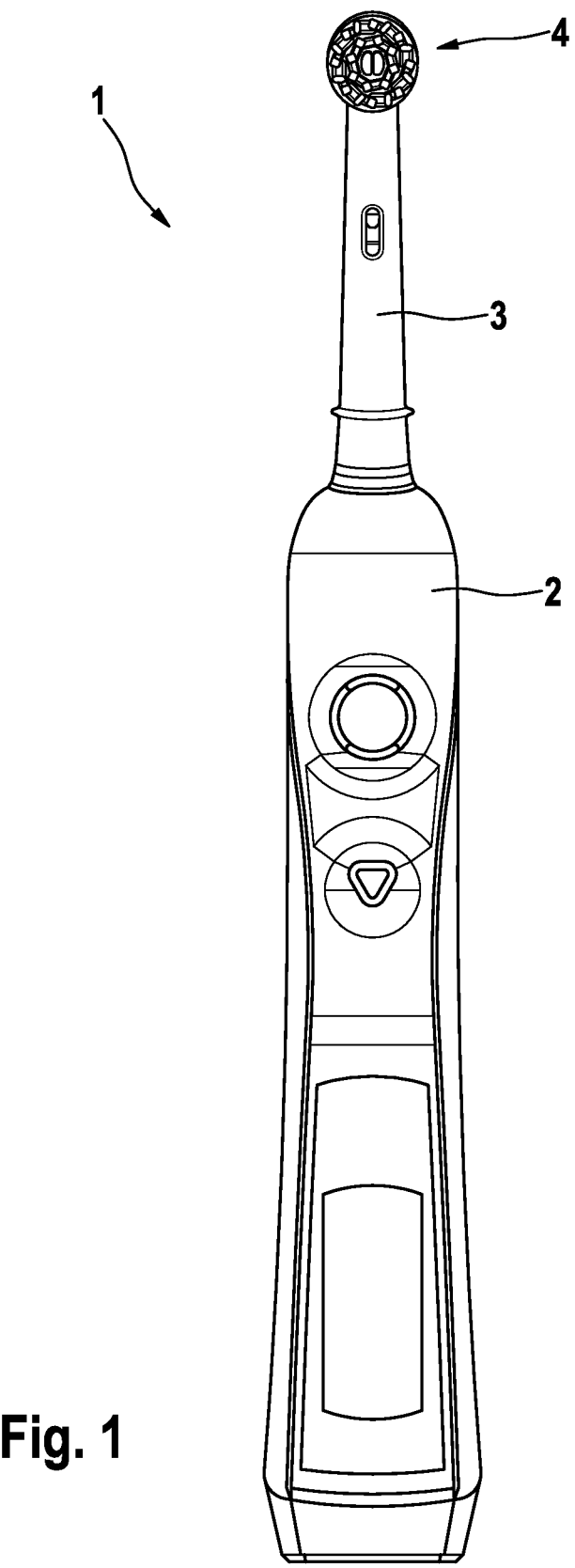
FIG. 1 is a depiction of an example embodiment of an electric device that may comprise a linear motor in accordance with the present disclosure.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

Although the embodiments are described herein in the context of an electric oral hygiene device, such as an electric toothbrush, embodiments are not limited thereto. Embodiments disclosed herein may be implemented in a wide-variety of applications, such as in the application of an electric tongue cleaner, an electric massage device and many others.

In some embodiments, a linear motor in accordance with the present description has an armature mounted for driven linear oscillation essentially along a longitudinal direction, a secondary mass mounted for linear oscillation essentially along the longitudinal direction, and a coupling unit for coupling the armature and the secondary mass, wherein the coupling unit comprises at least two coupling spring assemblies and at least a coupling element, the coupling spring assemblies being arranged in planes perpendicular to the longitudinal direction and being spaced apart from each other, and the coupling element being fixedly connected with the coupling spring assemblies.

As is known in the art, such a linear motor where a secondary mass is functionally coupled with a driven armature, the secondary mass can provide for an overall reduction of vibrations transmitted by the linear motor to its housing. Additionally or alternatively, the vibrations transmitted from the secondary mass to the housing may cancel the vibrations transferred from the armature to the housing at least to a certain fraction and ideally completely. This effect can in particular be seen if the armature and the secondary mass move with opposite amplitude (i.e. with a phase shift of about 180 degrees). If at least two coupling spring assemblies are used, this allows for distributing the amplitude of the movement of armature and secondary mass to these two coupling spring assemblies. Thus, the use of at least two spaced planar coupling spring assemblies such as flat leaf springs allows for using the same kind of spring assemblies for mounting of the armature and/or the secondary mass as then the coupling spring assemblies do not need to accommodate larger amplitudes than the mounting spring assemblies. In some embodiments, the armature is thus mounted by at least a first armature mounting spring assembly extending in a plane perpendicular to the longitudinal direction along which the armature is driven into a linear motion with respect to a housing of the linear motor and additionally or alternatively, the secondary mass is mounted with at least a first secondary mass mounting spring assembly extending in a plane perpendicular to the longitudinal direction with respect to the housing of the linear motor. In some embodiments, the spring assemblies of the linear motor all have the same shape and orientation and are superimposed when seen in the longitudinal direction.

In some embodiments, the mass of the armature and the mass of the secondary mass are chosen to be approximately identical, for example, the two masses do not differ by more than about 10%, in another embodiment by not more than about 5%, in a further embodiment by not more than about 2% and in an even further embodiment, by not more than about 1%. In some embodiments, the mass of the secondary mass and the mass of the armature are identical. In some embodiments, the mass of the coupling element is chosen to be at least a factor of about 10 smaller than the mass of either the secondary mass or the armature, in another embodiment wherein this factor is at least about 15. The smaller the coupling mass, the faster the transfer of changes of the motion of the armature to the secondary mass and thus the lower the residual vibrations that are not cancelled during these transient periods.

In some embodiments, a linear motor in accordance with the present description has an armature mounted for driven linear oscillation essentially along a longitudinal direction, a drive shaft being driven by the armature into a linear oscillation along a first longitudinal axis that is parallel to the longitudinal direction, wherein the armature is asymmetrically arranged with respect to the longitudinal axis and has two opposing end parts extending along the first longitudinal axis, a centre part comprising a permanent magnet arrangement, which centre part extends in longitudinal direction with an offset to the first longitudinal axis, and two connecting parts that each connect one of the end parts with the center part.

Such a particular design of the linear motor sensibly uses the available construction volume of a linear motor. In particular in case that the armature is mounted by leaf spring assemblies that have the respective fastening section in a centre area, the centre section of the armature needs to be retracted from the respective centre axis of the fastening locations to allow maximum construction volume for the stator that may be only arranged opposite to the armature. The back side of the centre section of the armature may then be as close as possible to the housing of the linear motor. As the end sections of the armature need to be fastened to the fastening section of the spring assemblies, the connecting sections connect the end parts with the retracted center section.

In some embodiments, a linear motor in accordance with the present description has an armature mounted for driven linear oscillation essentially along a longitudinal direction, and at least a first armature mounting spring assembly arranged in a mounting plane perpendicular to the longitudinal direction, wherein the first armature mounting spring assembly is shaped such that it fits into a circle approximating the shape of a half of the first armature mounting spring assembly in the mounting plane, where at least a first section of the circle can be cut away, which first section does not comprise a part of the first armature mounting spring assembly, the height of the first section being at least about 10% of the diameter of the circle, in another embodiment at least about 20% of the diameter, and in yet another embodiment at least about 25% of the diameter.

Additional or alternative aspects of a linear motor in accordance with the present disclosure are described in the following, in particular with reference to FIG. 2, FIG. 4 and FIG. 5. The term "spring assemblies" in the present disclosure is used to mean all spring assemblies of a linear motor as proposed, i.e. this term may include at least a first armature mounting spring assembly, at least a first secondary mass mounting spring assembly, and/or at least a first coupling spring assembly; the term "mounting spring assemblies" thus is used to mean all mounting spring assemblies, i.e. this term may include at least a first armature mounting spring assembly and/or at least a first secondary mass mounting spring assembly. Each of the spring assemblies may be realized by a leaf spring or by a stack of leaf springs. The leaf springs may be planar in a rest state (i.e. when they are not deformed) and may thus extend in a plane (neglecting the thickness of the leaf spring or of the stack of leaf springs). The leaf springs may in particular have a spiral-like structure, i.e. the leaf spring may comprise a spring arm that spirals from a centre area of the leaf spring to an outer area. In particular, a radial beam in the plane of extension of the leaf spring originating from the centre of area of the leaf spring may for all angles (i.e. about 0 degrees to about 360 degrees) always cross the spring arm at least once. In accordance with at least one aspect of the present disclosure, all spring assemblies may have the same shape and may be arranged with identical orientation. While the mounting spring assemblies may be fixed at one end with respect to the motor housing, the coupling spring assemblies may not be fixed at any end with respect to the motor housing. In accordance with at least one aspect of the present disclosure, the shape of the spring assemblies in at least a half of the leaf spring may be approximated by a circle from which a section is cut away, where the height of the section is at least about 10% of the diameter of the circle, in another embodiment at least about 15% of the diameter, in yet another embodiment at least about 20% of the diameter, and in yet another embodiment at least about 25% of the diameter, even though higher values are not excluded, for example, at least about 30%, at least about 35% etc. As the shape of the spring assemblies may essentially define the cross sectional shape of the linear motor, such a shape provides additional construction volume in parallel to the linear motor in case the linear motor is disposed in a housing (of a handle section of an electric device) having an inner cavity that is essentially circular in cross section. Additional or alternative aspects of spring assemblies in accordance with the present disclosure are described in the following, in particular with reference to FIG. 3.

FIG. 1 shows an example embodiment of an electric device 1 in accordance with the present disclosure, here realized as an electric toothbrush, which electric device 1 may comprise a linear motor in accordance with the present disclosure. The electric device 1 may comprise a handle section 2 and a detachable attachment section 3 that is shown in an attached state, i.e. in a state where the attachment section 3 is attached to the handle section 2. The attachment section 3 may comprise a first connector structure and the handle section 2 may comprise a second connector structure (see FIG. 4 for reference) enabling a detachable connection between attachment section 3 and handle section 2, for example, the attachment section 3 may comprise two flexible snap hooks and the handle section 2 may comprise two respective depression into which snap noses of the snap hooks can engage. The attachment section 3 may in particular include a functional element 4, for example, a brush head, which brush head may be mounted for driven movement. As will be explained in the following, the linear motor may be disposed in the handle section 2 and may comprise a drive shaft that is functionally coupled with the functional element 4 in the attached state so that the drive shaft transfers motion provided by the linear motor during operation to the functional element 4. For example, the linear motor may provide a linear oscillatory motion via the drive shaft, which linear oscillation is transferred to the functional head 4 and may be converted by a respective gear unit into an oscillatory rotation of the functional element 4 around a rotation axis that may be essentially perpendicular to a longitudinal axis along which the drive shaft vibrates. Of course, other movements of a functional element may be contemplated, for example, an oscillatory wiping motion around an axis that is essentially parallel to the longitudinal axis, a rotation or oscillatory rotation around a rotation axis that is angled with respect to the longitudinal axis etc. Instead of being realized as an electric toothbrush, the electric device 1 may be for example, another oral hygiene device such as an electric flossing device, an electric tongue scraper, an electric interdental cleaner, an electric tooth stick or as an electric skin treatment device such as an electric massage device or an electric exfoliation brush etc.

Figure 2:
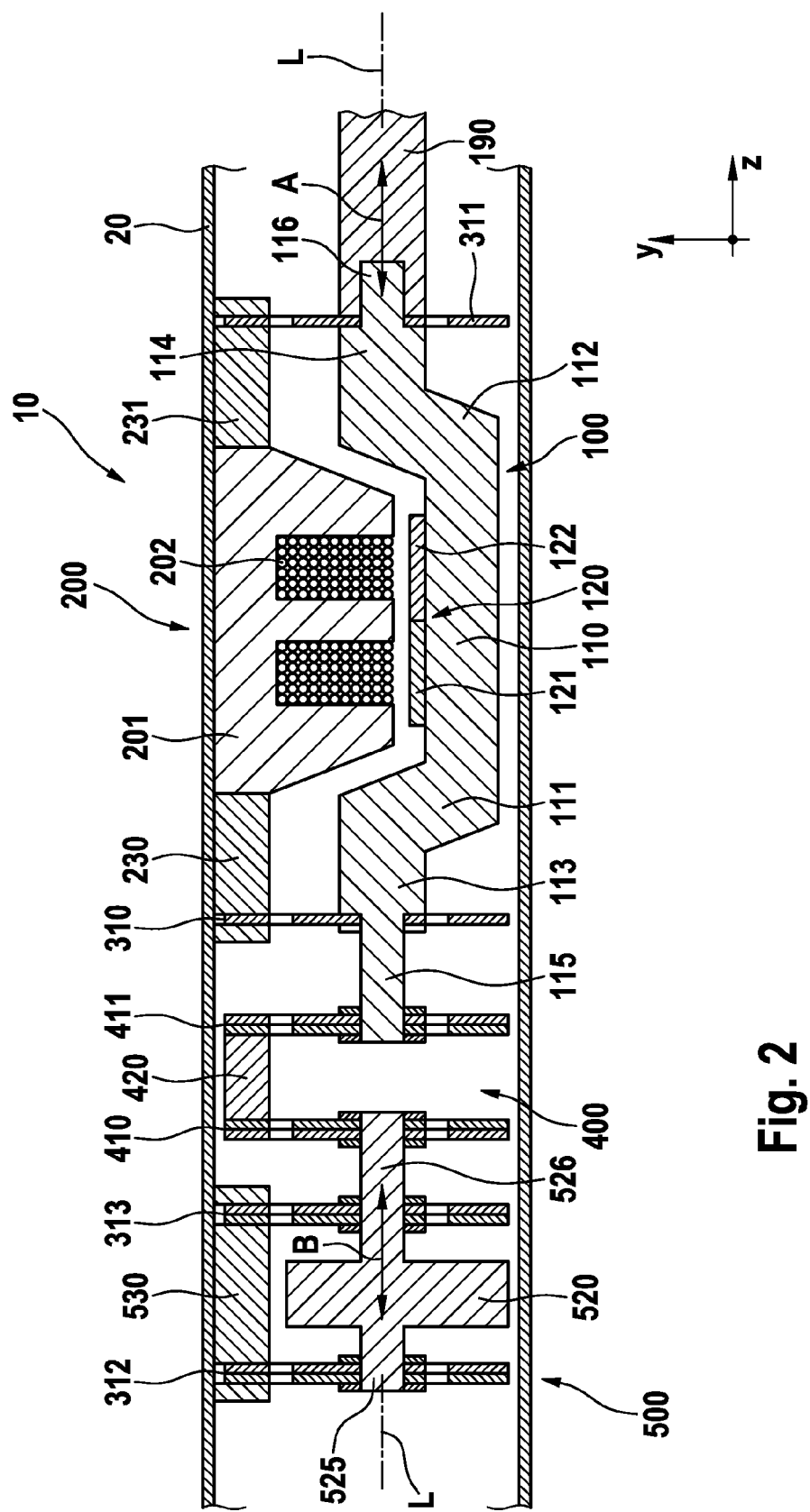
FIG. 2 is a longitudinal cut through an example embodiment of a linear motor in accordance with the present disclosure.

FIG. 2 is a longitudinal cut through an example embodiment of a linear motor 10 in accordance with one or more aspects of the present disclosure. The linear motor 10 may be utilized in an electric device 1 as discussed in connection with FIG. 1. The linear motor 10 may have a motor housing 20, an armature 100 mounted for linear oscillation along a longitudinal direction (which is parallel to a longitudinal axis L indicated in FIG. 1) as indicated by double arrow A, a stator 200, a secondary mass unit 500 mounted for linear oscillation along the longitudinal direction as indicated by double arrow B, and a coupling unit 400 for mechanically coupling the armature 100 to the secondary mass unit 500. A Cartesian coordinate system is indicated, where the z axis coincides with the longitudinal axis L and the y axis is perpendicular to the z axis in the paper plane. The x axis extends into the paper depth.

The stator 200 comprises a coil core 201 that may be fixedly connected with the motor housing 20 and a stator coil 202 wound around the coil core 201. While in FIG. 2 an E-shaped (i.e. three-toothed) back iron is shown, this shall not exclude that other back-iron designs may be utilized, for example, a U-shaped (i.e. two-toothed) back iron. The teeth of the coil core 201 have end surfaces that face a permanent magnet arrangement 120 mounted at a centre section 110 of the armature 100. The linear motor 10 may comprise at least two electrical contacts for providing electric current to the stator coil 202 during operation. The coil core 201 may be made from a stack of isolated sheets such as ferromagnetic metal sheets ("soft iron", for example, Fe—Si based metal) as is known in the art. In some example embodiments, the length of the end surface of the centre leg of an E-shaped coil core in z-direction may be about 3.0 mm and the respective length of the end surface of the other two legs may be about 2.0 mm.

The armature 100 may also (at least partly) be made from a stack of isolated sheets such as ferromagnetic metal sheets (for example, Fe—Ni based metal) as is known in the art. The armature 100 may be mounted at the housing 20 by means of at least one armature mounting spring assembly 310, 311 and the secondary mass unit 500 may be mounted at the motor housing 20 by means of at least one secondary mass mounting spring assembly 312, 313. In the shown example embodiment, the armature 100 is mounted at the housing 20 by means of two armature mounting spring assemblies 310 and 311 and the secondary mass 520 is mounted at the housing by means of two secondary mass mounting spring assemblies 312 and 313. The coupling unit 400 comprises two coupling spring assemblies 410 and 411 and a coupling element 420. The coupling element 420 may be fixedly connected to the coupling spring units 410 and 411. In one embodiment, the armature mounting spring assemblies 310 and 311, the secondary mass mounting spring assemblies 312 and 313 or the coupling spring units 410 and 411 may be realized as leaf springs that may each extend in a rest state in a plane being perpendicular to the longitudinal axis L, which leaf springs may have a spiral-like shape with a first fastening section being arranged at the outside of the spring and a second fastening section being arranged more in a center area of the spring (an example topology for such a leaf spring will be discussed with reference to FIG. 3 further below).

Each of the mounting spring assemblies 310, 311, 312, 313 may be at one end (i.e. with a first fastening section) fixedly connected at or with relation to the motor housing 20 and at another end (i.e. at a second fastening section) fixedly connected with the armature 100 or the secondary mass unit 500, respectively. As shown in FIG. 2, each of the mounting spring assemblies 310, 311, 312, 313 may be mounted at the motor housing 20 by means of a fastening element 230, 231, or 530, which fastening elements may each be fixedly mounted at the motor housing 20 and may be fixedly mounted at the first fastening section of the respective mounting spring assembly. Each of the mentioned spring assemblies 310, 311, 312, 313, 410, or 411 may be made from a single leaf spring or from a stack of (in particular identically shaped) leaf springs stacked in z direction. Each of the leaf springs may have a certain thickness in z direction to achieve a target spring constant. The thickness and the number of the leaf springs may be set to tune the characteristics of the components of the linear motor 10 such as the resonance and anti-resonance (or: cancellation) frequencies (the anti-resonance or cancellation frequency is the frequency at which the armature and the secondary mass do not only move with essentially opposed phase but also with essentially identical amplitude such that the vibrations transferred to the motor housing are minimal). While a high spring constant could be achieved by a thick leaf spring instead of a stack of two thinner leaf springs, it has been found that a thicker leaf spring has a different deflection curve than a stack two thin leaf springs and that the latter has a better fatigue resistance and thus may improve the long life behavior of the overall motor design. The coupling unit 400 and its coupling spring assemblies 410 and 411 determine, for example, the speed of the transfer of changes of the armature movement to the secondary mass. As the two oscillating systems, namely the first system comprising armature 100 together with the respective armature mounting spring assemblies 310 and 311 and the second system comprising the secondary mass unit 500 and the respective secondary mass mounting spring assemblies 312 and 313, are strongly coupled, the resonance frequencies of the two systems are strongly dependent. In one embodiment, the armature 100 may have fastening protrusions 115 and 116 that extend in z direction and that are centrically disposed with respect to the longitudinal axis L. As shown in FIG. 2 for an example embodiment of a linear motor in accordance with the present disclosure, the left-side (where left and right are used with respect to the paper plane on which the linear motor is depicted) fastening protrusion 115 may be fixedly connected with the left-side armature mounting spring assembly 310 and, displaced in longitudinal direction to the left, with the right-side coupling spring assembly 411. Further, the right-side fastening protrusion 116 may be fixedly connected with the right-side armature mounting spring assembly 311. Additionally, the right-side fastening protrusion 116 may establish a connection with a drive shaft 190 such that the linear oscillation of the armature 100 indicated by double arrow A is transferred during operation to the drive shaft 190 and from the drive shaft 190 to a functional element to be driven into motion (as explained with reference to FIG. 1). The drive shaft 190 may be centrically disposed with respect to the longitudinal axis L.

Further, the secondary mass 520 may have fastening protrusions 525 and 526 that extend in z direction (i.e. in longitudinal extension direction) and that are centrically disposed along the longitudinal extension axis L. The right-side fastening protrusion 526 may be fixedly connected with the right-side secondary mass mounting spring assembly 313 and, displaced in longitudinal direction to the right side, with the left-side coupling spring assembly 410. Further, the left-side fastening protrusion 525 may be fixedly connected with the left-side secondary mass mounting spring assembly 312.

The whole assembly of armature 100 (together with the respective armature mounting spring assemblies 310 and 311), coupling unit 400 and secondary mass unit 500 essentially forms a three-mass oscillator (neglecting here that the armature may be connected via the drive shaft with a further at least partly springy attachment section that will be driven during operation and also assuming that the housing vibrations may cancel each other completely so that the housing mass can also be neglected). As will be explained in more detail below, the secondary mass unit 500 is utilized to be excited into a counter-oscillation with respect to the armature oscillation during operation. Thus, the vibrations transferred to the motor housing 20 (and thus to the handle section of the electric device in which the linear motor 10 is mounted) will on the one hand be reduced over a design without a secondary mass unit 500 and the vibrations transferred to the housing will on the other hand at least partially cancel each other out due to the counter-phase oscillation of the secondary mass unit 500 with respect to the oscillation of the armature 100. In order to achieve that changes in the oscillation of the armature 100 (for example, due to load applied at the linear motor 10) are quickly transferred to the secondary mass unit 500 such that the counter-oscillations can reduce the vibrations felt by a user holding the handle section of the electric device, the coupling unit 400 may be made lightweight, for example, the coupling element 420 may be made lightweight. While materials such as hard plastic or wood may be lightweight, they may not be easily connectable with the coupling spring assemblies 410, 411. Thus, the coupling element 420 may be made of metal which can be welded with for example metal leaf springs, which may form the coupling spring assemblies 410, 411, but the coupling element 420 may be designed with a small volume to achieve a lightweight design. Other joining technologies besides welding are also considered, for example riveting or grouting. The length extension (i.e. the extension along the z axis) of the coupling element 420 may be chosen such that the distance between the two coupling spring assemblies 410 and 411 in z direction is such that on both sides a leaf spring deformation of the maximal amplitude of the armature 100 can be allowed without that the coupling spring assemblies 410 and 411 touch each other (the length setting may need to take into account that the respective fastening protrusions 115 and 526 need to extend into the space between the coupling spring assemblies 410 and 411 for fastening reasons and may further take into account a security spacing).

The armature 100 may comprise several sections, namely two end sections 113 and 114, one centre section 110 and two intermediate sections 111 and 112 that each connect one end of the centre section 110 with a respective end section 113 or 114, i.e. the left intermediate section 111 connects the left end of the centre section 110 with the left end section 113 and the right intermediate section 114 connects the right end of the centre section 110 with the right end section 114. While the left and right end sections 113 and 114 may be centrically disposed around the longitudinal axis L, which has a certain distance to the motor housing 20, the center section 110 is disposed with only a small distance to the motor housing 20, i.e. the center section 110 extends along a longitudinal axis that is parallel to the longitudinal axis L and that lies closer to the motor housing 20. Hence, the center section 110 is retracted towards one side of the motor housing 20 so that more construction volume is made available between the center section 110 and the opposite side of the motor housing 20. In contrast to other linear motor designs known from electric toothbrushes where the stator is arranged around the armature, this particular design of the armature 100 as discussed allows arranging the stator 200 opposite to the center section 110 of the armature 100 at the opposite side of the motor housing. A permanent magnet assembly 120 is disposed on a side of the centre section 110 of the armature 100 that faces the end surfaces of the teeth of the coil core 201. In one embodiment, the permanent magnet assembly 120 includes two abutting permanent magnets 121 and 122 that are arranged side-by-side in z direction. In an example embodiment, the permanent magnets may have a height in x-direction of about 1.3 mm, a width in z-direction of about 11.5 mm, and a length in y-direction of about 6.0 mm. The permanent magnets may be made from (sintered) FeNdB (neodymium-iron-boron) material.

In particular, an air gap between the end surfaces of the coil core 201 and the permanent magnet arrangement 120 may extend close to, approximately centrically with respect to the longitudinal axis L, which design may lead to lower tilting forces during operation, which supports using the mounting spring assemblies also as bearings for the armature. This leads on one hand to a more simple motor design, hence to a relatively low cost realization of the linear motor, and on the other hand to a design option that allows higher forces to be provided by the linear motor at a given construction volume (as will be discussed further below with reference to FIG. 4).

Figure 3:
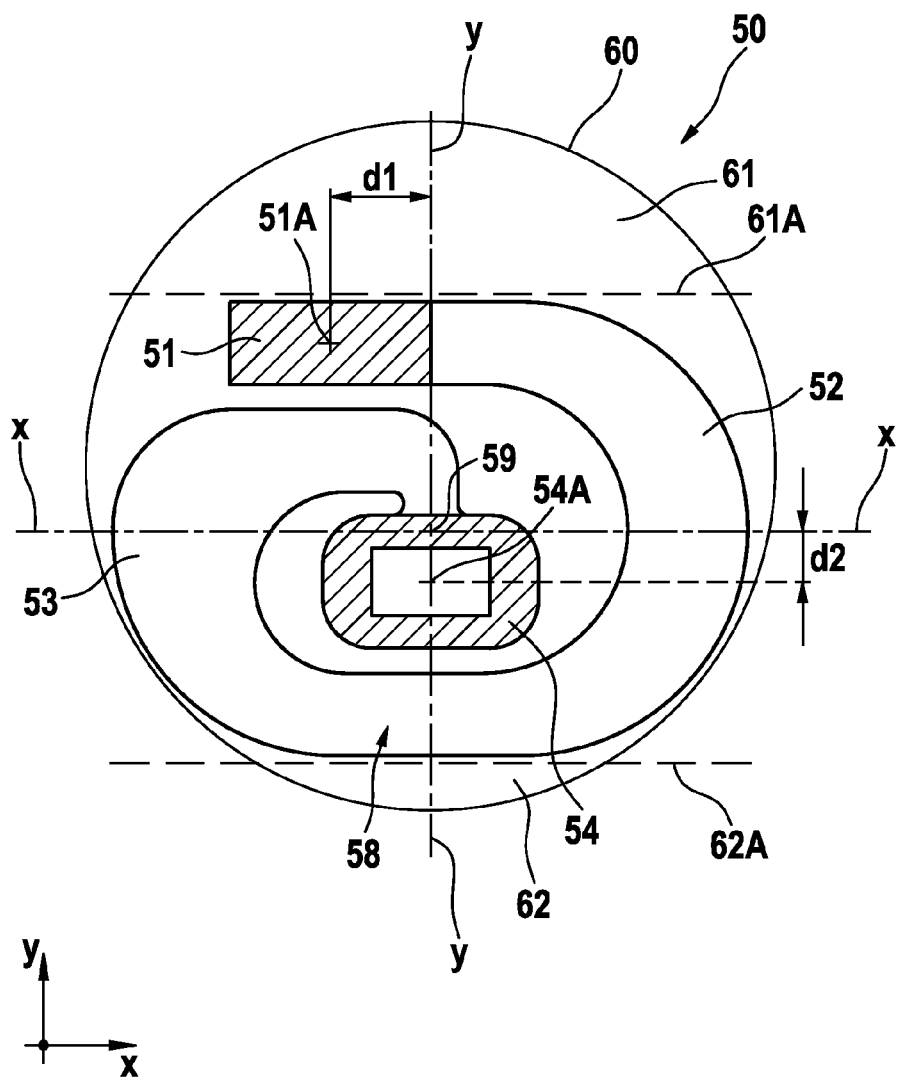
FIG. 3 is a depiction of an example embodiment of a leaf spring as it may be used in a linear motor in accordance with the present disclosure.
Figure 4:
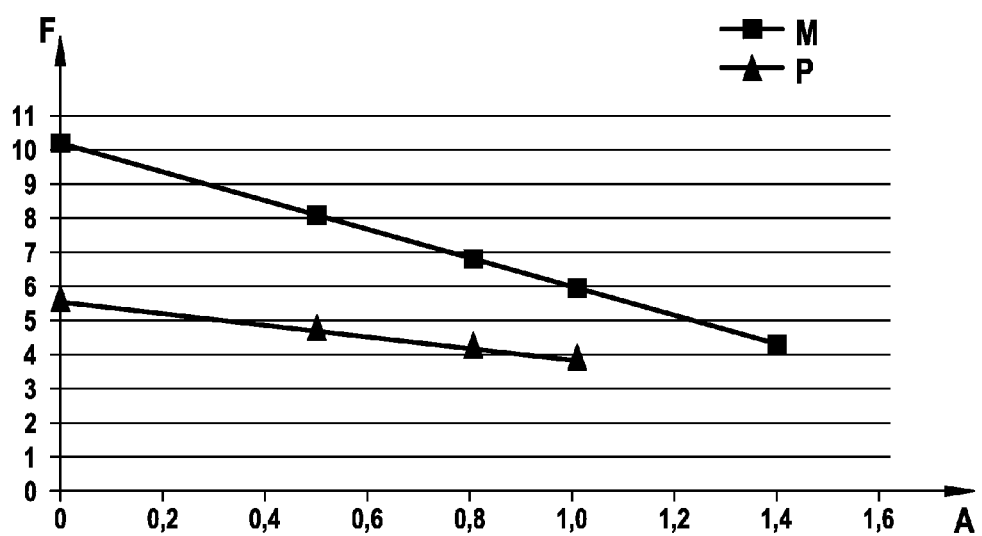
FIG. 4 is a graph indicating the maximum driving force F that may be provided by a linear motor versus the peak amplitude A of the linear oscillation, where the curve referenced as M relates to a motor in accordance with the present disclosure.

FIG. 3 is a depiction of an example embodiment of a leaf spring 50 that may be utilized in a linear motor as proposed. FIG. 3 shows the topology of the leaf spring 50 in its plane of extension spanned by axes x and y. The leaf spring 50 may have a homogeneous thickness in z direction (i.e. in a direction that is perpendicular to the paper plane in which the leaf spring 50 is depicted). Such leaf springs as shown may in particular be made from a sheet of stainless steel, for example by stamping or laser cutting, even though other materials, in particular other metal sheet materials such as brass shall not be excluded and also other manufacturing techniques such as cutting shall also not be excluded. In one embodiment, the leaf spring 50 has a generally spiral-like topology. The leaf spring 50 starts at a top left position with a first fastening section 51, then a spiral-like arm 58 follows that is composed of a first arm section 52 and a second arm section 53. The spiral-like arm 58 ends in a more central position close to a center of area 59 of the leaf spring 50 and is concluded by a second fastening section 54. Due to the spiral-like topology, the first fastening section 51 lies at the outside of the leaf spring and the second fastening section 54 lies more centric within the leaf spring area. That means that the drive coupling axis (i.e. longitudinal axis L as indicated in FIG. 2) is forced to lie near the centre of the leaf spring area if the first fastening section is used for fixation of the leaf spring 50 at a motor housing 20 (as shown in FIG. 2).

The shown example embodiment of a leaf spring 50 has various specific features that will be described in the following. For sake of clarity, a leaf spring for use in a linear motor as proposed may have none of these particular features, may have one, several or all of the described features.

With additional reference to FIG. 2, the first fastening section 51 may be either fastened to one of the fastening elements 230 or 530 and may thus become rigidly connected with respect to the motor housing 20 or may be fastened to the coupling element 420 and may thus become rigidly connected with the coupling element 420. The second fastening section 54 may be fastened to the armature 100 (for example, via one of the fastening protrusions 115 or 116) or to the secondary mass 520 (for example, via one of the fastening protrusions 525 or 526) and may thus become rigidly connected with the armature 100 or secondary mass 520, respectively.

Thus, the first and second fastening sections 51 and 54 are in a mounted state connected with parts that will move relatively to each other. The spring constant of the leaf spring 50 can be influenced by its dimensions (i.e. its width in x direction, its height in y direction and its thickness in z direction) and its topology. Further, in order to set a particular spring constant, two or more leaf springs 50 may be stacked in z direction to form a leaf spring assembly (as had been discussed previously with reference to FIG. 2), which spring leaf assembly then provides a spring constant that could otherwise only be provided by a much larger single leaf spring (larger in its x and y extensions or by a much thicker leaf spring as the spring constant is proportional to the spring volume). The leaf spring 50 allows for a movement of the first and second fastening sections 51 and 54 relative to each other in z direction under a given spring constant $k_z$ that acts to bring the leaf spring 50 back into a single extension plane. The spring constants $k_x$ and $k_y$ acting in x and y direction, respectively, are much larger than the spring constant $k_z$. Thus, utilization of the leaf spring 50 or leaf spring assemblies of two or more leaf springs 50 in a linear motor as shown in FIG. 2 lead not only to return forces acting in z direction against displacement of the armature 100 or the secondary mass 520 from their respective rest positions, but also allow for mounting of the armature 100 and the secondary mass 520 at the motor housing 20 without any further bearings such as ball bearings or slide bearings.

The center of area 51A of the first fastening section 51 may be offset to the y axis by a distance d1, where in some embodiments, d1 may be in the range of between about 0.1 mm to 10 mm. Additionally or alternatively, the center of area 54A of the second fastening area 54 may be offset from the x axis by a distance d2, where in some embodiments, d2 may be in the range of between about 0.1 mm to about 10 mm. These offsets of the first and/or the second fastening sections 51 and 54 may in particular be useful to increase the overall length of the spiral-like arm 58 over designs where at least one of the first and second fastening sections is not offset and thus these offsets likely lead to changes, for example an improvement of the spring characteristics of the leaf spring 50 for the intended use.

The spiral-like arm 58 has in both, its first and second arm sections 52 and 53 varying widths (where the width is measured in a direction perpendicular to a center line going from the first fastening section to the second fastening section), where the width of the first arm section increases from a start value of the width close to the first fastening section to a center width more or less at its maximum extension in x direction that may be increased with respect to the start width by about 50%. The initial start width may be again reached where the first radial arm extend most in y direction, i.e. where the first arm section 52 merges into the second arm section 53. The maximum width of the second arm section 53 may actually increase to a value of about 200% (or more) of the start width. Further, the width of the second arm section may become lower, for example by about 25% of the start width where the second arm section 53 merges into the second fastening section 54. The exact design and topology may be found by numerical simulation for a given linear motor design and the changes in the radial width of the spiral-like arm 58 may in particular be chosen to minimize stress in the leaf spring 50 during operation and thus this optimization has a positive influence on the wear of the leaf spring 50. The values given here with respect to the example embodiment shown in FIG. 3 are exemplary only and any other values may as well be considered, depending on the particular shapes, dimensions, and materials and on the oscillation amplitudes the leaf springs have to withstand.

At least one half of the leaf spring 50 may be approximated by a circle 60 drawn in the plane within which the whole leaf spring lies such that at least one section 61 of the circle can be cut away from the circle or such that two sections 61, 62 can be cut away from the circle by two parallel lines 61A, 62A (in the shown embodiment, these two parallel lines may be parallel to the x axis) so that the remaining shape still comprises the whole leaf spring. The height of each of the cut-away sections in y direction (assuming that the lines are parallel to the x axis) may be in a range of between about 1% to about 100% of the radius of the smallest possible circle. While the cut-away sections may have equal or similar height in y direction, the cut-away height may in particular be chosen to be different, for example, the relative cut away height for a leaf spring topology as shown in FIG. 3 may be about 5% for the lower section (i.e. in the negative y range) and about 30% for the upper section (i.e. in the positive y range). As the outer shape of the linear motor housing can follow the shape of the leaf springs (which means that all the other parts shown in FIG. 2 also have to fit into this shape defined by the leaf springs), this may result in free construction space inside of a more circular shaped housing of a electric device in which the linear motor will be contained. Thus, the flattened circular cross section of the linear motor may leave construction space inside of the housing of the electric device that can be used for, for example, accommodating a (optionally flexible) printed circuit board or other parts of the electric device.

In some embodiments, the leaf springs may be made from spring steel (material number 1.4310) and the thickness of the individual leaf springs may be between about 0.35 mm (for the mounting spring assemblies) and about 0.4 mm (for the coupling spring assemblies).

In the following, the operation of a linear motor as proposed is described, where reference is made to the example embodiments shown in FIG. 2 and FIG. 3, which should not be interpreted as limiting. In operation, an alternating coil current is applied from an energy source via a motor control circuit to the stator coil 202. An alternating electromagnetic field develops around the stator 200 that interacts with the permanent magnet arrangement 120 of the armature 100 and leads to an alternating (i.e. oscillatory) linear movement of the armature 100. The alternating coil current provided to the stator coil 202 may have a frequency at or close to the anti-resonance (or: cancellation) frequency of the overall oscillating system. The respective anti-resonance frequency (or frequencies) may, for example, be determined empirically or by means of numerical simulations. The linear motor 10 may be designed in a way that a typical maximum amplitude value of the linear armature oscillation lying in a range of between about ±0.1 mm to about ±2.0 mm is achieved when providing a maximally available current. In one embodiment, this range may be chosen to be between about ±0.5 mm to about ±1.5 mm, in another embodiment between about ±0.8 mm to about ±1.2 mm. In some embodiments, the maximum amplitude value may be chosen to be about ±1.0 mm.

It is stated here that the use of leaf springs as shown in FIG. 3 essentially confine the possible movement of the armature 100 to an oscillatory linear movement in z direction. Nevertheless, the deformation the leaf springs 50 shown in FIG. 3 (or other spiral-like leaf springs) experiences during operation will inevitably lead to a slight side motion of the second fastening section 54. One may now arrange one of the armature mounting spring assembly 310, 311 in the orientation as shown in FIG. 3, but the other armature mounting spring assembly in a mirrored (with respect to the y axis) orientation to compensate the side motion. But such an arrangement would likely lead to a skewing of the armature 100 with respect to the z axis. In contrast, in case that the armature mounting spring assemblies 310 and 311 would be mounted with identical orientation, this would lead to an overall side motion of the armature 100, which is likely to be a better controllable movement (in terms of the overall design of the electric device in which the linear motor shall be used) than any skewing movement.

The driven linear oscillations of the armature 100 is transferred to the secondary mass 520 (which is mounted by the secondary mass mounting springs 312 and 313 at the motor housing 20) via the coupling unit 400. Assuming that the excitation frequency of the applied stator coil current is predetermined accordingly, a counter-phase oscillation of the secondary mass 520 can thereby become excited, which counter-phase oscillation is at least close to 180 degrees phase shifted to the oscillatory movement of the armature 100.

The coupling unit 400 enables the vibration transfer from the armature 100 to the secondary mass 500. As has been stated previously, it is known to couple an armature and an amplitude spindle by a coil spring. Instead of a coil spring, the coupling unit 400 of the example embodiment shown in FIG. 2 utilizes two leaf spring assemblies 410 and 411. While it shall not be excluded that the coupling unit is realized by a single leaf spring, which has one fastening section that is fixedly connected with an end of the secondary mass and that has another fastening section that is fixedly connected with an end of the armature, such a realization of the coupling unit has certain features that will be discussed in the following. Firstly, the two mentioned fastening section would need to be at different locations, which would make the overall design more asymmetric, and thus it would likely become more prone to tilting forces. Secondly, the single leaf spring would need to accommodate a twice as long deformation in z direction as the leaf springs shown in FIG. 2, as the counter-phase movement of armature and the secondary mass add together. Such a double deformation distance in z direction can only be achieved with the same linear spring constant behavior by twice the leaf spring area. Thus, using two leaf springs for the coupling unit distributes the deformation over two leaf springs and these could be made identical in form (besides their thickness) to the mounting spring assemblies.

The overall oscillatory movement of the linear motor 10 may be in an equilibrium state after some 3 to 50 oscillations, depending on the particular design of the coupling unit 400.

It is known to utilize linear motors in oral hygiene device such as the Oral-B™ Pulsonic, where the linear motor drives a replacement brush head that is attached to a drive shaft providing linear oscillations having an oscillation amplitude of about ±0.5 mm into a respective linear oscillatory movement at a frequency of about 255 Hz. The linear motor of the Oral-B™ Pulsonic has a volume of about 18.4 cm$^3$ and can provide a maximum driving force during operation of about 4.5 Newton (N) and gets locked if a force of about 5.5 N is applied at the linear motor (as will be seen below with reference to FIG. 4). In contrast, a linear motor as proposed can be realized having a volume of about 14.8 cm$^3$ (48.5 mm length, 21 mm width, and 14.5 mm height), which linear motor can provide via its drive shaft a linear oscillation having an oscillation amplitude of about ±1.0 mm at a frequency of about 150 Hz and can provide a maximum driving force during operation of about 6.0 N and may get locked if a force of about 10.0 N is applied at the linear motor. The respective motor behavior is shown in FIG. 4, where the force (F) vs. amplitude (A) diagram can be seen for the two mentioned motors (where P indicates the Oral-B™ Pulsonic motor and M indicates the example embodiment of a proposed motor defined in this paragraph). The force F relates to the maximum current setting allowed for the respective motor. In FIG. 4 it can be seen that motor P provides a maximum force F of about 4.5 N at a peak amplitude value of about 0.5 mm and that motor M provides a maximum force of about 6 N at a peak amplitude of about 1.0 mm. With increasing applied force at the motor, the provided amplitude breaks down. For the previously known motor P, an applied force of 5.5 N will lead to a fully locked motor and no amplitude will be provided anymore. For the here discussed and proposed motor M, the motor would become locked at an applied force of 10 N. Thus, motor M can not only be used to drive a replacement brush head into linear oscillatory movement but also to drive a functional element mounted at the housing of a replacement brush into a movement different to a linear oscillatory motion, i.e. a motion that requires a gear unit and thus needs to overcome additional load. One aspect enabling the high force of the proposed linear motor in comparison to a known motor having similar or even higher volume is the particular motor design discussed with reference to FIG. 2.

Tests have been performed with an electric toothbrush as electric device utilizing a linear motor as proposed that is disposed in a handle section and an attachment section having as functional element a known replacement brush head (for example Oral-B™ Precision Clean) mounted for oscillatory rotation around an axis that is perpendicular to the longitudinal axis along which the linear motor vibrates. Firstly, it had been found that a linear motor providing a linear oscillatory movement having an amplitude of about ±1.0 mm around a rest position can drive the brush head into an oscillatory rotation having an angular amplitude of about ±20 degrees around a rest position, which ±20 degrees represents the angular amplitude provided by current electric toothbrushes such as the Oral-B™ Professional 5000 being equipped with an Oral-B™ Precision Clean. The angular amplitude of ±20 degrees was identified by sensory tests as a value that was preferred by at least a subgroup of test candidates also for the higher frequency of about 150 Hz against a frequency of about 75-85 Hz. Secondly, it had been found that a maximum driving force of 6 N at a peak amplitude value of ±1.0 mm is required to provide a good cleaning result for such an electric toothbrush. At a lower driving force, the angular peak amplitude breaks down from ±20 degrees too fast under regular cleaning conditions.

Figure 5:
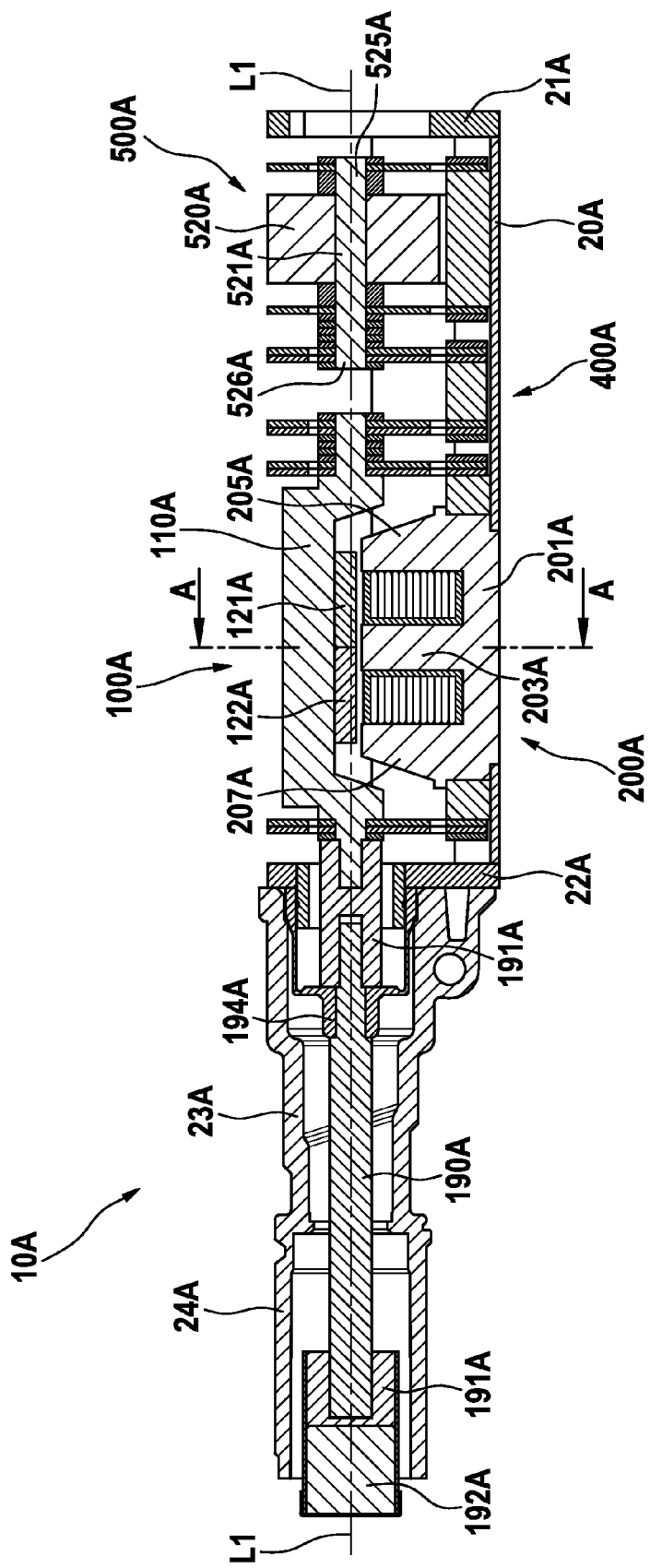
FIG. 5 is a longitudinal cut through an example embodiment of a linear motor including a drive shaft.

FIG. 5 is a longitudinal cut through an example embodiment of a linear motor 10A that is similar to the linear motor shown in FIG. 2 and additionally comprises a drive shaft assembly arranged in a tubular motor housing extension. The linear motor 10A depicted in FIG. 5 has an armature 100A mounted for driven linear oscillation along a longitudinal direction, a stator 200A arranged opposite to the armature 100A, and a secondary mass unit 500A coupled to the armature 100A via a coupling unit 400A. Two permanent magnets 121A and 122A are mounted at a central section 110A of the armature 100A such that end surfaces of the permanent magnets 121A, 122A face end surfaces of three legs 203A, 205A, 207A of an E-shaped coil core 201A. In a rest state, the end surface of the centre leg 203A of the coil core 201A is arranged centrically between the end faces of the two permanent magnets 121A, 122A. The armature 100A is coupled to a drive shaft 190 via a coupling adapter 190A. The drive shaft is centrically aligned with a longitudinal axis L1, which longitudinal axis L1 is parallel to the longitudinal direction along which the linear oscillation of the armature occurs. An air gap between the end surfaces of the permanent magnets 121A, 122A and of the end faces of the legs of the coil core is arranged to be close to the longitudinal axis L1, in particular the vertical centre line of the air gap may deviate from the longitudinal axis L1 by not more than about 1 mm, and in another embodiment by not more than about 0.5 mm.

As is best shown in the embodiments of FIGS. 2 and 5, the permanent magnet arrangement, comprising two permanent magnets (121, 122 in FIGS. 2 and 121A and 122A in FIG. 5) can be arranged asymmetrically with respect to the longitudinal axis so that the free end surface of the permanent magnet arrangement faces the stator, and more specifically one side of the stator. In the embodiments of FIGS. 2 and 5, the permanent magnets' free end surface faces the stator in a single direction ("Y" or "vertical" in FIGS. 2 and 5). In other words, the free end surface which is substantially planar in the embodiments of FIGS. 2 and 5) of the permanent magnet arrangement is adjacent to only one side of the stator—as opposed to circumferentially (or otherwise) surrounding, or partially surrounding the stator, as is common in cylindrical and rotational devices. Then, the armature's central section 110 (FIG. 2), 110A (FIG. 5), including the permanent magnet arrangement disposed thereon, can be offset from the longitudinal axis so that the free end surface of the permanent magnet arrangement and the longitudinal axis are in close proximity to one another. In the embodiment of FIG. 2 there is an air gap between the longitudinal axis L and the free end surface of the permanent magnets 121, 122; while in the embodiment of FIG. 5 the longitudinal axis L1 runs through the permanent magnets 121A, 122A.

The stator 200A is fixedly connected with a motor housing 20A. The motor housing 20A comprises a bottom cap 21A and a top cap 22A for added stability of the motor housing 20A. The drive shaft 190A extends in a hollow of a generally tubular front housing 23A that ends in an connection section 24A, which may comprise a connector structure suitable to establish an in particular mechanical connection with a respective connector structure at an attachment section (as was also explained with reference to FIG. 1). The drive shaft 190A has at its free end (opposite to its end where it is coupled to the armature 100A) a holder section 191A that may accommodate a magnetic coupling element 192A for establishing a magnetic connection with a respective magnetic coupling element of an attachment section such that the drive shaft 190A can transfer the linear oscillation provided by the armature 100A to a functional element mounted at the attachment section for driven movement. A bellows seal 194A may be arranged between the drive shaft 190A and the front housing 23A.

Figure 6:
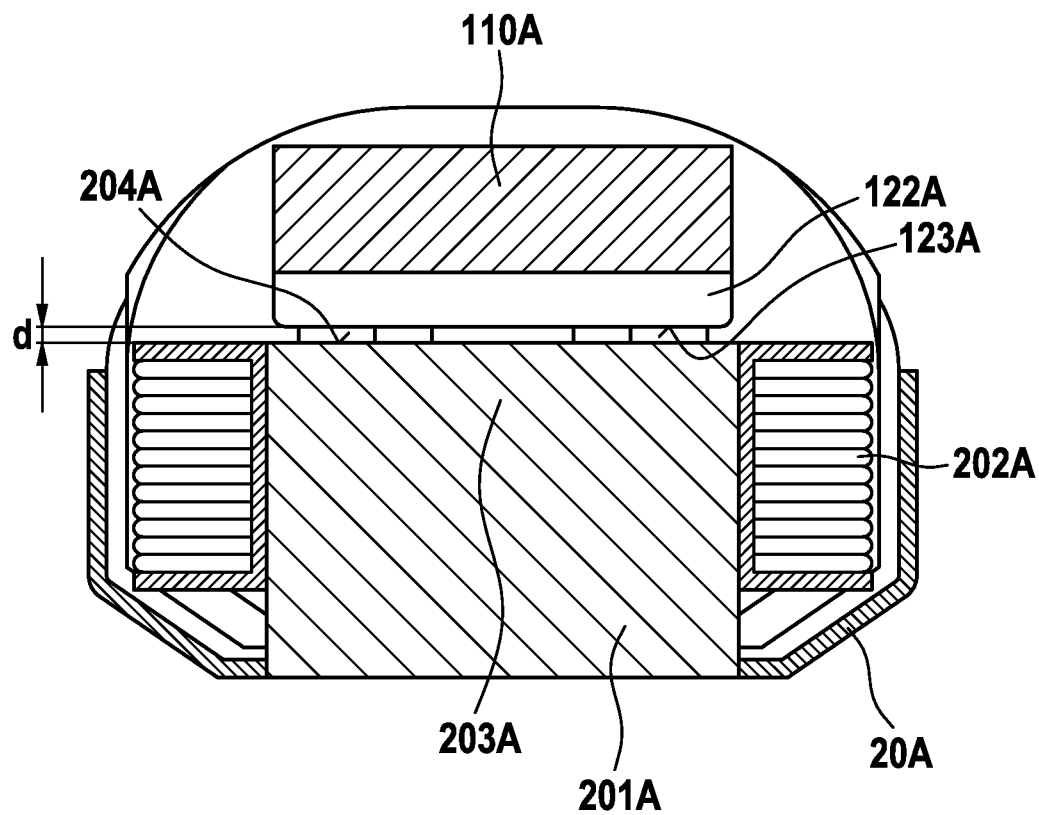
FIG. 6 is a cross sectional cut through the linear motor shown in FIG. 5 along the plane indicated by line A-A in FIG. 5.

FIG. 6 is a cross-sectional cut through the linear motor 10A shown in FIG. 5 along the plane that is indicated by line A-A in FIG. 5 with view direction towards the drive shaft. The cross sectional cut goes through the center section 110A of the armature at which the second permanent magnet 122A is mounted, which second permanent magnet 122A has an surface 123A that faces the end surface 204A of the center leg 203A of the coil core 201A. The end surface 204A of the center leg 203A and the end surface 123A of the second permanent magnet 122A are arranged with an air gap between them, which air gap may have a width d that may be in a range of between about 0.1 mm to about 0.6 mm, in yet another embodiment in a range of between about 0.2 mm to about 0.5 mm, and in yet a further embodiment in a range of between about 0.25 mm to about 0.4 mm. The stator coil 202A is wound around the center leg 203A of the coil core 201A.

FIG. 5 shows that the particular opposite arrangement of the stator 200A and of the armature 100A allows for optimally using the width of the cross sectional shape of the linear motor 10A, which cross sectional shape is essentially defined by the shape spring assemblies. Thus, the linear motor as proposed can provide a higher maximum driving force than other linear motors having the same construction diameter and volume but where a different motor design such a concentric arrangement is employed.

After the above description of example embodiments of a linear motor as described, it is stated again that various aspect of the linear motor are considered as independent aspects of the present disclosure. These aspects relate to (a) the design of the leaf springs as discussed with reference to FIG. 3 and the symmetric mounting rule (i.e. mounting the leaf springs with identical orientation), (b) the design of the system comprising the armature and the stator as discussed in particular with reference to FIGS. 2 and 5, (c) the design of the coupling unit as discussed in particular with respect to FIG. 2, and (d) the flattened circular cross-sectional shape of the linear motor.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An oral hygiene device with a resonant linear motor for providing a linear oscillatory movement along a longitudinal direction comprising:
    a housing;
    a stator comprising a coil core and a stator coil wound around the coil core, which stator is fixedly mounted at or with respect to the housing;
    an armature comprising a permanent magnet arrangement, which armature is mounted for linear oscillatory movement along the longitudinal direction relative to the stator, wherein the permanent magnet arrangement is arranged asymmetrically with respect to the longitudinal axis and has a free end surface facing one side of the stator; and
    a drive shaft coupled with the armature, the drive shaft centrically extending along a longitudinal axis parallel to the longitudinal direction;
    wherein the armature has two opposite end sections that are disposed at the longitudinal axis and a central section carrying the permanent magnet arrangement, which central section is offset from the longitudinal axis,
    wherein the resonant linear motor comprises a secondary mass mounted within the housing for linear oscillation along the longitudinal axis to reduce or cancel vibrations transferred from the armature to the housing, and a coupling unit for coupling the armature and the secondary mass, wherein the coupling unit comprises at least two spring assemblies and at least one coupling element, the spring assemblies being arranged in planes substantially perpendicular to the longitudinal direction and being spaced apart from one another, and the coupling element being fixedly connected to the spring assemblies.

2. The oral hygiene device according to claim 1, wherein the stator has at least one stator leg having an end face arranged to face the free end surface of the permanent magnet arrangement.

3. The oral hygiene device according to claim 2, wherein an air gap extends between the end surface of the stator leg and the end surface of the permanent magnet arrangement, which air gap is arranged close to the longitudinal axis, wherein a distance between a center line of the air gap and the longitudinal axis is below about 2.0 mm.

4. The oral hygiene device according to claim 3, wherein the minimal height of the air gap measured between the end surface of the stator leg and the end surface of the permanent magnet arrangement in a direction perpendicular to the longitudinal direction is in a range of between about 0.1 mm and about 0.6 mm.

5. The oral hygiene device according to claim 1, wherein the stator is arranged only opposite to the permanent magnet arrangement.

6. The oral hygiene device according to claim 1, wherein the armature is mounted via first and second armature mounting spring assemblies, wherein each of the armature mounting spring assemblies comprises at least one flat leaf spring.

7. The oral hygiene device according to claim 6, wherein the armature is only borne by the armature mounting spring assemblies.

8. The oral hygiene device according to claim 6, wherein the first and the second armature mounting spring assemblies are each arranged to extend in a plane perpendicular to the longitudinal direction and the armature and the stator are shaped such that they essentially fit into an area defined by the first and second mounting spring assemblies when viewed along the longitudinal direction.

9. The oral hygiene device according to claim 1, wherein the resonant linear motor further comprises a secondary mass unit mounted for linear oscillation along the longitudinal direction.

10. The oral hygiene device according to claim 1, wherein at least one of the spring assemblies is fixedly connected to the armature and at least one other of the coupling spring assemblies is fixedly connected to the secondary mass.

11. The oral hygiene device according to claim 1, wherein the secondary mass is approximately identical to a mass of the armature.

12. The oral hygiene device according to claim 11, wherein the mass of the coupling element is at least a factor 10 lower than the mass of the armature or the secondary mass.

13. The oral hygiene device according to claim 1, wherein the armature is borne by at least a first armature-mounting spring assembly and the secondary mass is borne by at least a second mass-mounting spring assembly, and wherein all spring assemblies have essentially identical shape and are mounted with a same orientation.

14. The oral hygiene device according to claim 1, wherein each of the spring assemblies comprises a flat leaf spring having an inner fastening section, an outer fastening section, and a spring arm connecting the inner fastening section and the outer fastening section, wherein the flat leaf spring is made from a single sheet such that the inner fastening section, the spring arm, and the outer fastening section are integral with one another, wherein the spring arm spirals around a center of area of the inner fastening section and the flat leaf spring is oblate in its plane of extension such that a ratio between a width of the leaf spring and a height of the flat leaf spring has a value of at least about 1.33, the direction in which the height is measured being perpendicular to the direction in which the width is measured.

15. The oral hygiene device according to claim 14, wherein the spring arm spirals around the center of area of the inner fastening section over an angular range of at least about 360 degree.

16. The oral hygiene device according to claim 14, wherein the center of the inner fastening section is positioned asymmetrically with respect to a height of the spring and symmetrically with respect to a width of the spring.

* * * * *